United States Patent [19]
Arndt et al.

[11] 4,418,204
[45] Nov. 29, 1983

[54] METHOD FOR MAKING ESTERS

[75] Inventors: Peter J. Arndt, Seeheim-Jugenheim; Joachim Lowitz, Alsbach-Haehnlein; Manfred Müller, Rossdorf; Fritz Schlosser, Darmstadt-Kranichstein, all of Fed. Rep. of Germany

[73] Assignee: Röhm GmbH, Darmstadt, Fed. Rep. of Germany

[21] Appl. No.: 422,253

[22] Filed: Sep. 23, 1982

[30] Foreign Application Priority Data

Oct. 14, 1981 [DE] Fed. Rep. of Germany ....... 3140764

[51] Int. Cl.$^3$ .......................................... C07D 301/00
[52] U.S. Cl. .................................................. 549/539
[58] Field of Search ......................................... 549/539

[56] References Cited

U.S. PATENT DOCUMENTS

| | | | |
|---|---|---|---|
| 2,537,981 | 1/1951 | Edwards | 260/348 |
| 2,556,075 | 6/1951 | Erickson | 260/88.3 |
| 4,074,062 | 2/1978 | Murakami et al. | 560/217 |
| 4,228,084 | 10/1980 | Ackermann et al. | 549/539 |
| 4,285,872 | 8/1981 | Tanabe et al. | 549/539 |

FOREIGN PATENT DOCUMENTS

| | | |
|---|---|---|
| 2423405 | 11/1975 | Fed. Rep. of Germany . |
| 2602157 | 7/1976 | Fed. Rep. of Germany . |
| 2088971 | 1/1972 | France . |
| 47-38421 | 9/1972 | Japan . |
| 1118206 | 6/1968 | United Kingdom . |

*Primary Examiner*—Norma S. Milestone
*Attorney, Agent, or Firm*—Curtis, Morris & Safford

[57] ABSTRACT

What is disclosed is a method for the transesterification of lower alkyl esters of α,β-unsaturated acids such as acrylic and methacrylic acid, with an epoxy alcohol, such as glycidol, which uses 1,4-diazabicyclo(2,2,2)octane as a transesterification catalyst.

5 Claims, No Drawings

METHOD FOR MAKING ESTERS

The present invention relates to a method for the preparation of esters of carboxylic acids with alcohols containing epoxy groups by the transesterification of other esters of carboxylic acids, and more particularly the preparation of esters of acrylic and methacrylic acid with 2,3-epoxy-1-propanol.

The transesterification (alcoholysis) of lower acid esters with higher alcohols is a widely used method of producing the corresponding higher acid esters.

The method is suited also for the conversion of unsaturated esters, particularly of esters of α-β-unsaturated acids. For example, transesterification is used for the preparation of higher esters of acrylic and methacrylic acid, the starting product usually being methyl esters produced on a commercial scale. In addition to alkali metal alcoholates and orthotitanic acid esters, acid catalysts such as paratoluenesulfonic acid or sulfuric acid are suited for use in the alcoholysis of methyl acrylate and methyl methacrylate.

Various processes have been proposed for the preparation of esters containing epoxy groups, which latter are industrially used as crosslinking monomers, in particular glycidyl acrylate and glycidyl methacrylate.

One process for the preparation of glycidyl esters, for example, is based on a reaction of the sodium or potassium salt of acrylic or methacrylic acid with epichlorohydrin (U.S. Pat. Nos. 2,556,075 and 2,537,981), optionally with the addition of catalytic amounts of tetramethylammonium chloride.

While it is possible to carry out the alcoholysis of acrylic or methacrylic esters with glycidol (2,3-epoxy-1-propanol) using alkali metal hydroxides as catalysts, this approach does not produce fully satisfactory results. For example, the catalyst will deposit as a sludge in the reaction sump of the alcoholysis mixtures. Sludge formation generally complicates the reaction considerably and interferes with the control of the process sequences. It is a nuisance especially in working up the product because it may require a filtration step. Above all, the use of alkali metal hydroxides as alcoholysis catalysts with the reactants named does not permit the high yields which are required in industrial processes to be obtained.

Thus there has been a need for carrying out the alcoholysis of lower alkyl ($C_1$–$C_4$) esters of acrylic acid or of methacrylic acid with glycidol to yield glycidyl esters in such a way that the method can be performed industrially with a minimum of process engineering equipment and with maximum yields.

It has now been found that the problem so defined can be solved by using 1,4-diazabicyclo (2,2,2)octane as a transesterification catalyst.

The amounts of 1,4-diazabicyclo(2,2,2)octane to be used usually range from 0.005 to 0.085 weight percent, preferably from 0.025 to 0.010 weight percent, and more particularly from 0.015 to 0.010 weight percent, based on the alcohol and ester used.

The conversion of lower alkyl esters, and in particular of the methyl ester of acrylic or methacrylic acid, with the catalyst dissolved therein, yields residue-free crude glycidyl esters which are directly distillable, for example in a thin-layer evaporator, without filtration.

Particularly advantageous is an embodiment of the process in accordance with the invention in which, in addition to 1,4-diazabicyclo(2,2,2)octane, alkali metal hydroxides, and in particular potassium hydroxide, are used in amounts which are decidedly lower than the amount of alkali metal hydroxides normally used to catalyze transesterification. Thus the concurrent use of from 25 to 100 ppm, and more particularly from 30 to 85 ppm, of an alkali metal hydroxide, and particularly potassium hydroxide, has been found to have a favorable effect on the outcome of the alcoholysis.

When alkali metal hydroxides are used in the low amounts indicated, filtration may likewise be dispensed with.

In the process of the invention, the lower alkyl ester of acrylic or methacrylic acid and the alcohol containing epoxy groups are generally used in a molar ratio ranging from 1:1 to 1:10, and preferably of 1:3.

The charge may further contain auxiliary agents such as stabilizers, for example, hydroquinone monomethyl ether, hydroquinone, phenothiazine, or N,N'-diphenyl-para-phenylenediamine.

The process may be carried out in the following manner, for example:

The lower acrylic acid or methacrylic acid ester, in particular methyl methacrylate, is charged together with the alcohol containing epoxy groups, more particularly glycidol, and the optionally added auxiliary agents, to a suitable reaction vessel, for example a round-bottomed flask using an agitator, heating means with a thermostat, an air inlet connection, and a column set onto it which inter alia is suited for the application of a vacuum, or is charged into a mixing kettle with a column.

Then a vacuum is applied and heating is started. The further procedure set forth below is based on the use of methyl methacrylate as the lower alkyl ester.

At a vessel temperature of about 60° C. (at a vacuum of about 200 millibars), the alcohol distillate (methyl methacrylate in azeotropic mixture with methanol) starts to pass over at an overhead temperature of about 30° to 36° C. As soon as no further alcohol distillate is observed, excess methyl methacrylate is drawn off at an increased overhead temperature (about 50° C.). By stepwise improvement of the vacuum, the residual crude ester can be substantially degassed, that is to say, freed of methyl methacrylate. The degassed crude ester can then be vacuum distilled. A pure product is obtained in a very good yield.

A better understanding of the present invention and of its many advantages, will be had by referring to the following specific examples, given by way of illustration.

EXAMPLE 1

A mixture of 70.0 kg (945 moles) of glycidol, 280 kg (2800 moles) of methyl methacrylate, 120 ppm of 1,4-diazabicyclo(2,2,2)octane, 30 ppm of KOH (in methanol), and 200 ppm of N,N'-diphenyl-para-phenylenediamine (as a stabilizer) is charged into a 500-liter V4A agitated vessel having a 4-meter steel column packed with porcelain Raschig rings and equipped with water and brine reflux condenser, interchangeable receiver, reflux control, and vacuum control. A vacuum is produced and the vessel is heated by means of circulating hot water. At a vessel temperature of 60° C. and an overhead temperature between 32° and 35° C., a distillate starts passing over from the alcoholysis with a reflux ratio of 2:1. The vessel temperature rises to 70° C., and the overhead temperature is held between 33° and 36° C. by adjustment of the reflux ratio of 5:1. As soon as no further alcoholysis distillate can be drawn off under these conditions, unreacted methyl methacrylate is withdrawn at a reflux ratio of 1:1 and a temperature of 50° C. Through stepwise improvement of the vacuum, the crude glycidyl methacrylate ester formed can be degassed down to a residual gas content of about 10%. After further degassing at 110° C. in the vapor space and a vacuum of 30 mm Hg, the ester formed can be distilled at 115° C. in the vapor space and 1 to 2 mm Hg. Yields over 80% are observed. The total time usually ranges from about 6 to 9 hours.

EXAMPLE 2

A mixture of 475 g (6,41 moles) of glycidol, 2000 g (20 Mol) of methyl methacrylate 200 ppm of 1,4-diazabicyclo(2,2,2)octane and 200 ppm of N,N'-diphenyl-p-phenylenediamine (as a stabilizer) is charged into a 4-liter agitated glass vessel having a 1 meter glass column packed with glass Raschig rings and equipped with a water and a brine reflux condenser, interchangeable receiver, reflux control and vacuum control. A vacuum is produced and the vessel is heated by means of circulating hot water. At a vessel temperature of 60° C. and an overhead temperature between 32° and 35° C., a distillate starts passing over from the alcoholysis with a reflux ratio of 2:1. The vessel temperature rises to 70° C., and the overhead temperature is held between 33° and 36° C. by adjustment of the reflux ratio of 5:1. As soon as no further alcoholysis distillate can be drawn off under these conditions, unreacted methyl methacrylate is withdrawn at a reflux ratio of 1:1 and a temperature of 50° C. Through stepwise improvement of the vacuum, the crude glycidyl methacrylate ester formed can be degassed down to a residual gas content of about 10%. After further degassing at 110° C. in the vapor space and a vacuum of 30 mm Hg, the ester formed can be distilled at 115° C. in the vapor space and 1 and 2 mm Hg. Yields over 80% are observed. The total time usually ranges from about 6 to 9 hours.

What is claimed is:

1. A method for making an ester of a carboxylic acid with an alcohol containing an epoxy group by the transesterification of another ester of said carboxylic acid with said epoxy alcohol in the presence of 1,4-diazabicyclo(2,2,2)octane as a transesterification catalyst.

2. A method as in claim 1 wherein said carboxylic acid is an α,β-unsaturated acid and the ester which is transesterified is a lower alkyl ester of such an acid.

3. A method as in claim 1 wherein said epoxy alcohol is 2,3-epoxy-1-propanol.

4. A method as in claim 1 wherein the methyl ester of acrylic or methacrylic acid is transesterified.

5. A method as in claim 4 wherein said epoxy alcohol is 2,3-epoxy-1-propanol.

* * * * *